United States Patent
Chodorowski-Kimmes et al.

(10) Patent No.: US 9,445,986 B2
(45) Date of Patent: Sep. 20, 2016

(54) COSMETIC COMPOSITION, COSMETIC TREATMENT METHOD AND COMPOUND

(75) Inventors: Sandrine Chodorowski-Kimmes, Senlis (FR); Nathalie Jager Lezer, Verrieres-le-Buisson (FR)

(73) Assignee: L'OREAL, Paris (FR)

( * ) Notice: Subject to any disclaimer, the term of this patent is extended or adjusted under 35 U.S.C. 154(b) by 159 days.

(21) Appl. No.: 13/520,399

(22) PCT Filed: Dec. 13, 2010

(86) PCT No.: PCT/FR2010/052695
§ 371 (c)(1),
(2), (4) Date: Aug. 16, 2012

(87) PCT Pub. No.: WO2011/080448
PCT Pub. Date: Jul. 7, 2011

(65) Prior Publication Data
US 2012/0315230 A1    Dec. 13, 2012

Related U.S. Application Data

(60) Provisional application No. 61/300,523, filed on Feb. 2, 2010.

(30) Foreign Application Priority Data

Jan. 4, 2010 (FR) ..................... 10 50012

(51) Int. Cl.
| A61K 8/92 | (2006.01) |
| A61Q 3/00 | (2006.01) |
| A61K 8/96 | (2006.01) |
| A61Q 17/04 | (2006.01) |
| A61Q 19/00 | (2006.01) |
| C07D 239/22 | (2006.01) |
| A61Q 5/00 | (2006.01) |
| A61Q 1/06 | (2006.01) |

(52) U.S. Cl.
CPC ............. *A61K 8/927* (2013.01); *A61Q 1/06* (2013.01)

(58) Field of Classification Search
CPC ............ A61K 8/92; A61K 8/96; A61K 8/44; A61K 8/27; A61Q 17/04; A61Q 1/046
See application file for complete search history.

(56) References Cited

U.S. PATENT DOCUMENTS 5,972,324 A * 10/1999 Zofchak et al. ......... 424/78.03
2004/0161394 A1    8/2004 Mougin et al.
2006/0018856 A1    1/2006 Bosman et al.
2007/0053859 A1 *  3/2007 Bui et al. ................... 424/63
2007/0093639 A1    4/2007 Jassen et al.
2010/0028277 A1    2/2010 Chodorowski-Kimmes et al.

FOREIGN PATENT DOCUMENTS

EP    2140858 A1    1/2010
FR    2825628 A1   12/2002

OTHER PUBLICATIONS

Lange H-bond Supra. Polym. J. Polym. Sci. A Polym. Chem. V 37 p. 3657 1999.*
Dankers et al., "A modular and supramolecular approach to bioactive scaffolds for tissue engineering", Nature Materials, vol. 4, No. 7, Jul. 2005, pp. 568-574.
Van Beek et al., "Supramolecuar Copolyesters with Tunable Properties," Macromolecules, vol. 40, No. 17, Jul. 31, 2007, pp. 6340-6348.
Folmer et al., "Supreamolecular Polymer Materials: Chain Extension of Telechelic polymers using a Reactive Hydrogen-Bonding Synthon", Advanced Materials, Wiley VCH Verlag, De Lnkd, vol. 12, No. 12, Jun. 16, 2000, pp. 874-878.

* cited by examiner

*Primary Examiner* — David J Blanchard
*Assistant Examiner* — Thurman Wheeler
(74) *Attorney, Agent, or Firm* — Polsinelli PC

(57) ABSTRACT

The invention relates to a cosmetic composition comprising, in a cosmetically acceptable medium, a compound that can be obtained by reaction between an OH-functionalized or COOH-functionalized wax and a junction group capable of establishing hydrogen bonds with one or more partner junction groups, said junction group comprising at least one unit of formula (I) or (II):

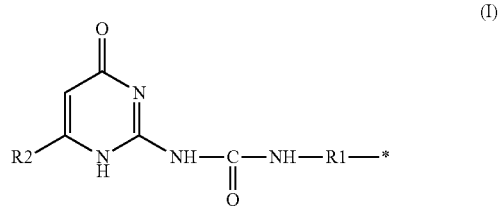

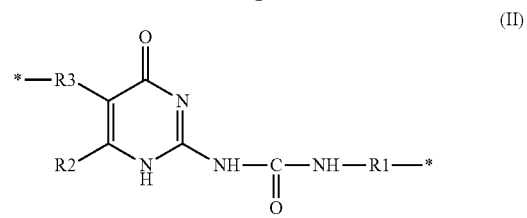

The invention also relates to a cosmetic treatment process using said compounds.

19 Claims, No Drawings

COSMETIC COMPOSITION, COSMETIC TREATMENT METHOD AND COMPOUND

CROSS REFERENCE TO RELATED APPLICATIONS

This application is a National Phase filing under 35 U.S.C. §371 of PCT/FR2010/052695 filed on Dec. 13, 2009; and this application claims priority to Application No. 1050012 filed in France on Jan. 4, 2010, and this application claims the benefit of U.S. Provisional Application No. 61/300,523 filed on Feb. 2, 2010, under 35 U.S.C. §119; the entire contents of all are hereby incorporated by reference.

The present invention relates to a cosmetic composition comprising a compound obtained by reaction between a functionalized wax and a junction group, and also to a cosmetic treatment process using said composition, and to said compounds.

In many cosmetic compositions, waxes are used as a mixture with oils and other fatty substances, in order to give some body to the compositions. These compositions find applications mainly in the skin and/or hair makeup and/or care field. Waxes are commonly used to give the compositions texture and they generally have great stability over time.

However, problems of mechanical stability and/or of compatibility between waxes and volatile products, in particular the volatile oils generally present in cosmetic compositions, can arise. For a low wax content, insufficient hardness of the composition, stick for example, is in fact noted, which may be responsible for problems of stability or in relation to use. Simply increasing the proportion of hardening waxes does not make it possible to solve these problems, since this is generally reflected by a degradation of the cosmetic properties of the product, which becomes uncomfortable to wear.

Indeed, in certain cases, the compositions may have a tacky feel and the feel of a fatty deposit and can be difficult to apply, in particular when they comprise amounts of waxes that are too great. Furthermore, the deposit formed on the keratin support may be uneven, especially at a high wax concentration.

One of the objectives of the present invention is to propose waxes which make it possible to obtain appropriate hardening, i.e. which have an appropriate gelling power, so as to limit the amount of waxes in the cosmetic products and thus to avoid problems of incompatibility.

A subject of the present invention is therefore a cosmetic composition comprising, in a cosmetically acceptable medium, a compound that can be obtained by reaction between:

at least one wax bearing at least one reactive function chosen from OH or COOH, and at least one junction group capable of establishing hydrogen bonds with one or more partner junction groups, each pairing of a junction group involving at least 4 hydrogen bonds, said junction group bearing at least one "complementary" reactive function capable of reacting with the reactive function borne by the wax, said junction group comprising at least one unit of formula (I) or (II) as defined hereinafter.

The resulting compound forms another subject of the invention.

By functionalizing the wax with ureidopyrimidones, it is possible to obtain a homogeneous deposit on keratin materials, or even a deposit with properties close to a film, and thus to allow either the use of a small amount of waxes for an equivalent hardening, or a use at a high concentration without having a tacky or greasy effect on application.

The waxes functionalized according to the present invention are in the form of a solid; this makes it possible in particular to form a non-tacky material, which does not transfer to the finger once applied to a keratin substrate.

Moreover, it has been found that crosslinking by means of four hydrogen bonds, via ureidopyrimidone groups, can make it possible to increase the strength of this crosslinking, and thus to improve the wear property of the desired cosmetic effect, most particularly the wear property of the deposit.

Furthermore, the compounds, or functionalized waxes, according to the invention are easy to convey in the usual cosmetic media, in particular the usual cosmetic oily media.

They are easy to convey in cosmetic oily or solvent media, in particular oils, fatty alcohols and/or fatty esters, which facilitates their use in the cosmetic field, in particular in makeup. They show suitable solubility in varied cosmetic oily media, such as plant oils, alkanes, esters, whether they are short esters such as butyl or ethyl acetate, or fatty esters, and fatty alcohols, and most particularly in media comprising isododecane, Parleam, isononyl isononanoate, octyldodecanol and/or a $C_{12}$-$C_{15}$ alkyl benzoate.

The compounds according to the invention can be obtained by reaction between:

firstly, at least one wax bearing at least one reactive function chosen from OH or COOH, and secondly, at least one junction group capable of establishing hydrogen bonds with one or more partner junction groups, each pairing of a junction group involving at least 4 hydrogen bonds, said junction group bearing at least one "complementary" reactive function capable of reacting with the reactive function borne by the wax, in particular isocyanate, said junction group comprising at least one unit of formula (I) or (II) as defined hereinafter.

Finally, the compounds according to the invention thus comprise at least one part originating from the wax and at least one part (G) originating from the junction group, said part (G) comprising at least one unit of formula (I) or (II).

In particular, said parts are linked via a covalent bond, and in particular can be linked by a covalent bond formed during the reaction between the OH and/or COOH reactive functions borne by the wax and the complementary reactive functions, in particular isocyanate, borne by the junction group, capable of reacting with said OH and COOH functions.

The wax that may be used in the context of the present invention therefore bears at least one reactive function capable of reacting with the complementary reactive function borne by the junction group, and in particular capable of reacting chemically with the isocyanate groups borne by the junction group; preferably, this function is an OH or COOH function, or even a carboxylic acid anhydride function. Preferably, the wax bears only OH functions, preferentially primary or secondary OH functions, and even better still only primary OH functions.

The wax that may be used for preparing the compound according to the invention is a lipophilic fatty substance or a lipophilic fatty substance mixture, which is crystalline at 25° C., and solid at ambient temperature and under atmospheric pressure (25° C., 1 atm.); preferably with a reversible solid/liquid change of state and generally having a melting point above 40° C., better still above 55° C. and even better still above 75° C., and which can range up to 200° C., in particular up to 120° C. By bringing the wax to its melting point, it is possible to make it miscible with oils and to form a microscopically homogeneous mixture, but if the temperature of the mixture is brought back to ambient temperature, recrystallization of the wax from the oils of the mixture is obtained.

The waxes that may be used in the context of the present invention may be of plant, mineral, animal or synthetic origin.

They may be chosen from the following waxes, alone or as a mixture, it being understood that these waxes bear a reactive function, in particular an OH, COOH, or even anhydride reactive function:

(i) long-chain, generally linear, alcohols of formula $CH_3$—$(CH_2)_n$—OH with n between 13 and 60, in particular between 15 and 47, or even between 15 and 31.

Such fatty alcohols are commercially available, for example from the company New Phase Technologies or the company Petrolite. They may be mixtures of long-chain linear alcohols that can be obtained by means of a polymerization process which makes it possible to obtain polymers with a very low polydispersity index (Mw/Mn less than 1.1). Their weight-average molar mass (Mw) is generally between 350 and 1000. Mention may in particular be made of cetyl alcohol, stearyl alcohol and octacosanol;

(ii) saturated or unsaturated, generally linear, $C_8$-$C_{60}$ long-chain acids; mention may in particular be made of those of formula $CH_3$—$(CH_2)_n$—COOH with n between 6 and 58, in particular between 8 and 48, or even between 10 and 32; mention may also be made of $C_6$-$C_{60}$, or even $C_8$-$C_{32}$, monounsaturated or polyunsaturated fatty acids;

(iii) calcium lanolates or stearates;

(iv) lanolin and derivatives thereof, such as hydrogenated, hydroxylated or acetylated lanolin, lanolin alcohols, lanolin fatty acids and acetylated lanolin alcohol;

(v) polyolefin waxes, in particular poly(alpha-olefin) homopolymers and copolymers, preferably having a melting point above 25° C., preferably between 25 and 110° C., which are optionally polyoxyalkylenated ($C_2$-$C_3$ alkyl), optionally (poly)glycerolated, and which bear at least one functional group —OH, —COOH or carboxylic acid anhydride, for example -(polyoxyalkylene)$_n$-OH, or polyglycerol. Among these polyolefins, mention may be made of homopolymers and copolymers of $C_2$-$C_{30}$, preferably $C_2$-$C_{10}$, or even $C_2$-$C_3$, olefins. Polyethylene and polypropylene homopolymers, and their copolymers with one another or with another $C_4$-$C_{10}$ alpha-olefin, are in particular preferred. These polyolefins, preferably oligomers of Mw less than 10,000, can be obtained by means of the known polymerization techniques: radical polymerization, Ziegler-Natta polymerization, or using metallocene initiators.

In particular, mention may be made of:

polyethylene or polypropylene waxes, ending with an OH end group, such as the Performacol products sold by New Phase Technologies, in particular Performacol 350 (Mp 79° C.), 425 (Mp 91° C.) and 550 (Mp 99° C.);

polyoxyethylenated or polyoxypropylenated polyethylene or polypropylene waxes ending with a —(POE)-OH, —(PPO)—OH or —(POE)/(PPO)—OH end group, such as the Performatox Ethoxylate ethoxylated polyethylenes sold by New Phase Technologies, in particular Performatox Ethoxylate 420 (Mp 91° C.), 450 (Mp 91° C.), 480 (Mp 88° C.), 490 (Mp 71° C.), 520 (Mp 99° C.) and 550 (Mp 99° C.);

polyolefins, preferably polyethylene or polypropylene, which are glycerolated or polyglycerolated (bearing [O—$CH_2$—CH(OH)—$CH_2$]$_x$—OH groups, with x preferably between 1 and 50);

polyolefins, preferably polyethylene or polypropylene, bearing a COOH or carboxylic acid anhydride group; in particular polyethylenes or polypropylenes bearing a COOH end group such as the Performacid Acid products sold by New Phase Technologies, in particular Performacid Acid 350 (Mp 89° C.), 425 (Mp 93° C.), 550 (Mp 101° C.) and 700 (Mp 110° C.);

polyolefins, in particular ethylene and/or propylene homopolymers or copolymers, bearing one or more succinic anhydride groups along their chain and resulting from the addition of maleic anhydride on one or more residual unsaturations, or from direct olefin-maleic anhydride copolymerization, such as:

(i) polypropylenes comprising maleic anhydride groups (or succinic anhydride groups once attached to the chain), in particular Licocare PP207 from Clariant, (ii) polyethylenes comprising maleic anhydride groups, in particular Ethylene-Maleic Anhydride Copolymer from Honeywell, such as A-C 573 A (Drop point: 106° C.), A-C 596 A (Drop point: 143° C.); (iii) poly(isobutylene-maleic anhydride) copolymers, in particular those sold by Kuraray under the trade name Isobam; (iv) maleic anhydride/octadecene copolymers such as those sold by Chevron Phillips Company under the name PA18; (v) copolymers between long-chain olefins and maleic anhydride, such as Licocare CM 401 LP 3345 from Clariant;

(vi) natural waxes which have a large fraction of free fatty alcohols and/or of free fatty acids; among those comprising free fatty alcohols, mention may be made of candelilla wax, carnauba wax and sugarcane wax; among those comprising free fatty acids, mention may be made of beeswax, orange wax, montan wax, lemon wax and sugarcane wax;

(vii) polyoxyethylenated (bearing an end OH) or polyglycerolated (several side OHs and an end OH) "natural" waxes; these are natural or synthetic waxes which may have one or more residual COOHs which are reacted with an alcohol, dialcohol, polyol or ethoxylated alcohol, or a $C_2$-$C_4$ alkylene glycol (preferably glycerol) or polyglycerol; mention may in particular be made of:

polyoxyethylenated natural waxes (number of EO preferably between 2 and 100): PEG beeswax (Apifil from Gattefosse or PEG-8 Bee Wax from Koster Keunen), PEG candelilla Wax; PEG carnauba wax such as PEG-12 Carnauba from Koster Keunen; PEG lanolin; oxypropylenated lanolin wax; PEG spermaceti wax; PEG shellac wax;

glycerolated or polyglycerolated waxes: polyglycerolated beeswax, in particular polyglyceryl-3 beeswax (Cera Bellina Wax from Koster Keunen); the acacia decurrens/jojoba/sunflower seed wax/polyglyceryl-3 esters mixture (Hydracire S from Gattefosse);

(viii) silicone waxes, for instance polyether silicone waxes, and alkyl or alkoxy dimethicones having from 16 to 45 carbon atoms;

(ix) polyoxyalkylenated $C_{12}$-$C_{40}$ fatty alcohols, in particular bearing at least one $C_{12}$-$C_{40}$, in particular $C_{14}$-$C_{32}$, alkyl group, and a polyoxyalkylene, preferably polyoxyethylene and/or polyoxypropylene, group, with an OH end group; in particular polyoxyethylenated stearyl alcohol, and more particularly steareth-10 or polyoxyethylenated (10 EO) stearyl alcohol, steareth-2 or polyoxyethylenated (2 EO) stearyl alcohol and steareth-20 or polyoxyethylenated (20 EO) stearyl alcohol, and in particular Brij S10-SO, Brij S2-SO and Brij S20-SO from Croda; mixtures of oxyethylenated lanolin fatty alcohols, such as Solulan 16 Lanolin from Lubrizol; Tegocare 150 from Evonik, Emulcire 61 WL2659 from Gattefosse; isosteareth-20 or polyoxyethylenated (20 EO) isostearyl alcohol, such as Arosurf 66E20 from Witco; PEG-6 decyltetradeceth-30, in particular Nikkopol PEN-4630 from Nikko; PEG-6 decyltetradeceth-12, in particular Nikkol PEN-4612 from Nikko; PEG-4 montanate, in particular Licowax KST from Clariant; hydrogenated and polyoxyethylenated castor oils, such as PEG-7 hydrogenated castor oil and in particular Cremophor PH from BASF; the PEG-45/dodecylglycol copolymer and in particular Elfacos ST9 from Akzo;

(x) monoesters and multiesters between at least one polyol, including glycerol, and a $C_8$-$C_{40}$ mono fatty acid, bearing at least one free OH; and monoesters or multiesters between a polyol and a $C_8$-$C_{40}$ mono fatty alcohol. Mention may in particular be made, as fatty acid, of: stearic acid, behenic acid; as polyol bearing at least one residual OH: pentaerythritol, erythritol, di-pentaerythritol, trimethylolpropane, di-trimethylolpropane, glycerol, diglycerol, polyglycerols and sucrose. Mention may in particular be made of batyl alcohol or glyceryl monostearyl ether, and in particular Batyl Alcool 100 from Nikko; bis-diglyceryl polyacyladipate-2 (=isostearic, adipic and glyceryl plant fatty acid esters) such as Softisan 649 from Sasol; glycol montanate or octacosanoate, such as Licowax KPS Flakes from Clariant; pentaerythrityl distearate such as Cutina PES from Cognis; esters of sucrose and of a fatty acid with a residual OH, and in particular sucrose esterified with 6-8 behenic acid chains, comprising at least 2 free OHs, such as Cromaderm B from Croda; pentaerythrityl isostearate/caprate/caprylate/adipate with residual OHs, such as Supermol L-LQ(RB) from Croda, sucrose palmitate such as Surfhope SE COSME C-1615 from Mitsubishi; sucrose tribehenate such as Surfhope SE COSME C-2203 from Mitsubishi.

Mention may also be made, by way of preference, of monoesters or multiesters between at least one glycerol, monoglycerolated or polyglycerolated, and a $C_8$-$C_{40}$, in particular $C_{12}$-$C_{32}$, mono fatty acid, bearing at least one free OH; mention may in particular be made of polyglyceryl-10 behenate/eicosadioate such as Nomcort HK-P from Nisshin Oil; glyceryl behenate/eicosadioate such as Nomcort HK-G from Nisshin Oil; polyglyceryl-10 hydroxystearate/stearate/eicosadioate such as Nikkol Nikkowax LM from Nikko Chemicals; polyglyceryl-10 pentastearate (5 free OHs) such as Sunsoft Q-1855 from Taiyo Kagaku; glyceryl stearate such as Sunsoft 8000V from Taiyo Kagaku; glyceryl laurate such as Sunsoft 750 from Taiyo Kagaku; glyceryl behenate (mono-+dibehenate) such as Dub BG from Stearineries Dubois;

(xi) monoesters or multiesters between at least one $C_8$-$C_{40}$ polycarboxylic acid and one $C_8$-$C_{40}$ monoalcohol;

(xii) esters of a $C_8$-$C_{40}$ fatty acid and of a $C_8$-$C_{40}$ fatty alcohol, bearing in addition at least one OH group; and in particular:

esters of 12-hydroxystearic acid, with a $C_8$-$C_{40}$ monoalcohol, diol or polyol; in particular trihydroxystearin or glyceryl trihydroxystearate, such as Thixin R from Elementis; ethylhexyl hydroxystearate such as Wickenol 171 from Alzo; dipentaerythrityl hexahydroxystearate, such as Salacos 168M from Nisshin Oil; hydroxystearoyl stearate of $C_{18}$-$C_{38}$ fatty alcohols such as Kesterwax K82P from Koster Keunen; hydroxyoctacosanyl hydroxystearate such as Elfacos C26 from Akzo (which in the end bears 2 free OHs);

esters of hydrogenated ricinoleic acid with a $C_8$-$C_{40}$ monoalcohol, diol or polyol; in particular cetyl esters of hydrogenated castor oil fatty acids, such as Phytowax Ricin 16L 64 from Sophim;

esters or polyesters between hydrogenated castor oil (3 OHs) and a $C_8$-$C_{40}$ monoacid or diacid, retaining at least one of the three OHs of the hydrogenated castor oil molecule, and in particular the polycondensate between hydrogenated castor oil and isostearic and adipic acids, such as Haimalate 618 from Kokyu Alcohol;

esters of citric acid and of $C_8$-$C_{40}$ fatty alcohols, comprising at least one OH of the acid that is free; in particular tri($C_{14}$-$C_{15}$)alkyl citrate, such as Cosmacol ECL from Sassol.

A mixture of waxes may obviously be used.

Preferably, the waxes that can be used in the present invention are chosen from cetyl alcohol, beeswax, carnauba wax and jojoba wax, and mixtures thereof.

The junction group that can be used to form the compound according to the invention bears at least one reactive function that is complementary to the OH or COOH functions borne by the wax, in particular an isocyanate function. This function is capable of reacting with the OH and COOH reactive functions of the wax in order to form a covalent bond, in particular of urethane type, between said wax and said junction group.

Said junction group is capable of establishing H bonds with one or more partner junction groups, of identical or different chemical nature, each junction group pairing involving at least 4H (hydrogen) bonds.

For the purposes of the invention, the term "junction group" means any functional group comprising groups that are H bond donors or acceptors, and capable of establishing at least 3H bonds, preferably at least 4H bonds, preferentially 4H bonds, with an identical or different partner junction group.

For the purposes of the invention, the term "partner junction group" means any junction group that can establish H bonds with one or more junction groups of the same or of another polymer according to the invention. The junction groups may be of identical or different chemical nature. If they are identical, they may then establish H bonds between themselves and are then referred to as self-complementary junction groups. If they are different, they are chosen such that they are complementary with respect to H interactions.

Said junction group, bearing isocyanate groups, may thus be represented schematically as (G)-(NCO)$_p$, p being a non-zero integer, preferably equal to 1 or 2.

The junction group moreover comprises at least one monovalent unit of formula (I) and/or at least one divalent unit of formula (II), as defined below:

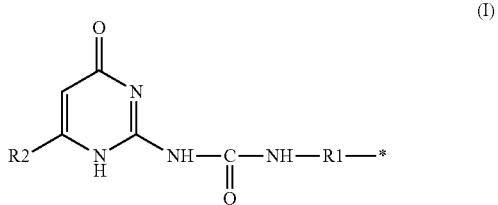

(I)

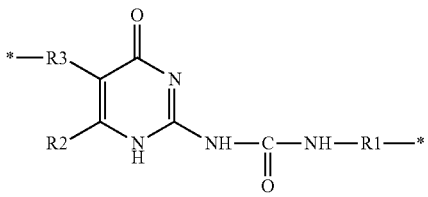

in which:

R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group; optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, $C_1$-$C_{32}$ carbon-based and in particular hydrocarbon-based (alkyl) radical, which may comprise one or more heteroatoms chosen from O, N, S, F, Si and P.

The radical R1 may in particular be:

a linear or branched, divalent $C_2$-$C_{12}$ alkylene group, in particular a 1,2-ethylene, 1,6-hexylene, 1,4-butylene, 1,6-(2,4,4-trimethylhexylene), 1,4-(4-methylpentylene), 1,5-(5-methylhexylene), 1,6-(6-methylheptylene), 1,5-(2,2,5-trimethylhexylene) or 1,7-(3,7-dimethyloctylene) group;

a divalent $C_4$-$C_{12}$ cycloalkylene or arylene group, chosen in particular from the following radicals: -isophorone-, tolylene, 2-methyl-1,3-phenylene, 4-methyl-1,3-phenylene; 4,4'-methylenebiscyclohexylene; 4,4-bisphenylenemethylene; or having the structure:

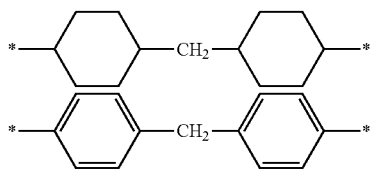

The term "-isophorone-" means the divalent radical having the structure:

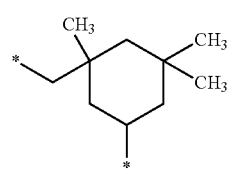 [SMILES: *CC1(C)CC(*)CC(C)(C)C1]

Preferentially, R1 represents -isophorone-, —(CH₂)₆— or 4,4'-methylenebiscyclohexylene.

The radical R2 may in particular be H or else:
a $C_1$-$C_{32}$, in particular $C_1$-$C_{16}$ or even $C_1$-$C_{10}$ alkyl group;
a $C_4$-$C_{12}$ cycloalkyl group;
a $C_4$-$C_{12}$ aryl group;
a $(C_4$-$C_{12})$aryl$(C_1$-$C_{18})$alkyl group;
a $C_1$-$C_4$ alkoxy group;
an arylalkoxy group, in particular an aryl$(C_1$-$C_4)$alkoxy group;
a $C_4$-$C_{12}$ heterocycle;
or a combination of these radicals, which may be optionally substituted with an amino, ester and/or hydroxyl function.

Preferably, R2 represents H, $CH_3$, ethyl, $C_{13}H_{27}$, $C_7H_{15}$, phenyl, isopropyl, isobutyl, n-butyl, tert-butyl, n-propyl, or else —CH($C_2H_5$)($C_4H_9$).

Preferably, R3 represents a divalent radical —R'3-O—C(O)—NH—R'4- in which R'3 and R'4, which may be identical or different, represent a divalent carbon-based radical chosen from a linear or branched $C_1$-$C_{32}$ alkyl group or a $C_4$-$C_{16}$ cycloalkyl group or a $C_4$-$C_{16}$ aryl group; or a mixture thereof.

In particular, R'3 and R'4 may represent methylene, 1,2-ethylene, 1,6-hexylene, 1,4-butylene, 1,6-(2,4,4-trimethylhexylene), 1,4-(4-methylpentylene), 1,5-(5-methylhexylene); 1,6-(6-methylheptylene); 1,5-(2,2,5-trimethylhexylene), 1,7-(3,7-dimethyloctylene); 4,4'-methylenebiscyclohexylene; 2-methyl-1,3-phenylene; 4-methyl-1,3-phenylene; 4,4'-bisphenylenemethylene; 1,2-tolylene, 1,4-tolylene, 2,4-tolylene, 2,6-tolylene; 1,5-naphthylene; tetramethylxylylene; isophorone.

Most particularly, R'3 may represent a $C_1$-$C_4$ alkylene, especially 1,2-ethylene. Preferably, R'4 may represent the divalent radical derived from isophorone.

Most particularly, R3 may have the structure:

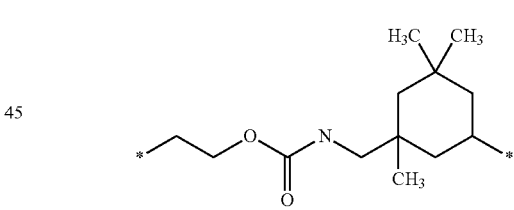

In a particularly preferred manner, the following may apply in formula (I):
R1=-isophorone-, R2=methyl, which gives the unit of formula:

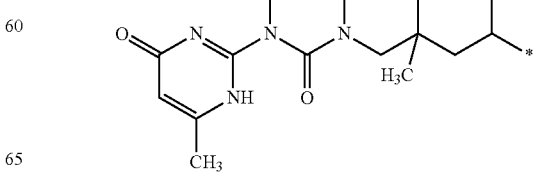

R1=—(CH$_2$)$_6$—, R2=methyl, which gives the unit of formula:

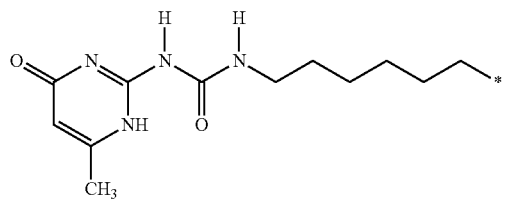

R1=—(CH$_2$)$_6$—, R2=isopropyl, which gives the unit of formula:

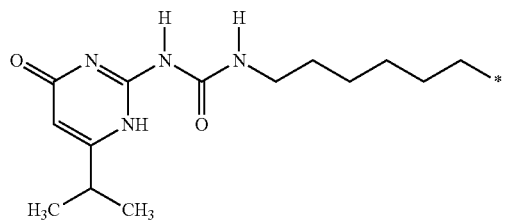

R1=4,4'-methylenebiscyclohexylene and R2=methyl, which gives the unit of formula:

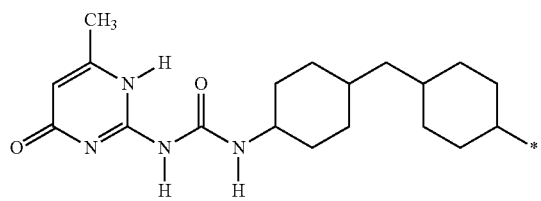

In a particularly preferred manner, in formula (II), R1 represents the -isophorone- radical, R2=methyl and R3=—(CH$_2$)$_2$OCO—NH-isophorone-, which gives the divalent unit of formula:

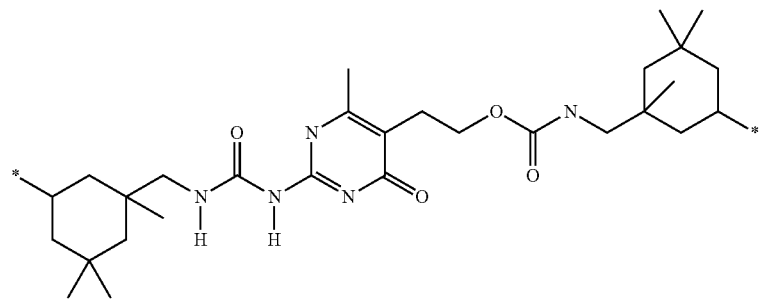

The junction groups bearing only one isocyanate function may have the formula:

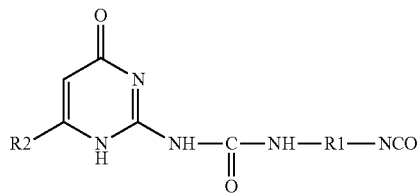

in which R1 and R2 are as defined above; and in particular:
R1 represents -isophorone-, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl, or else —CH(C$_2$H$_5$)(C$_4$H$_9$).

Preferably, the junction groups may be chosen from the following groups:

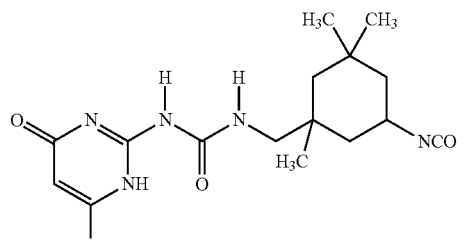

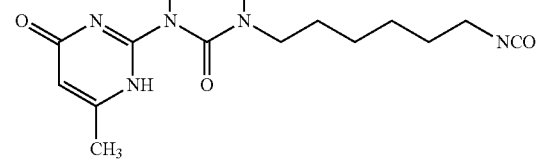

-continued

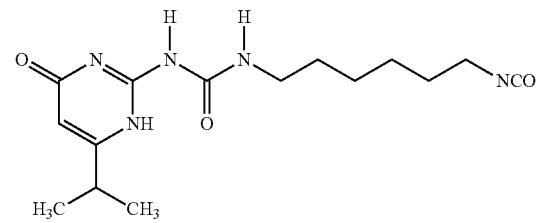

-continued

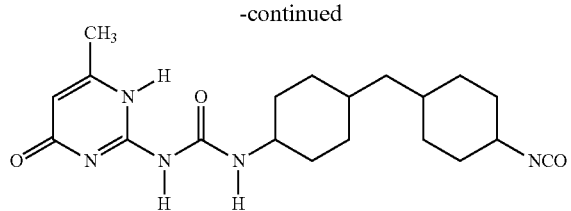

The junction groups bearing two isocyanate functions may have the formula:

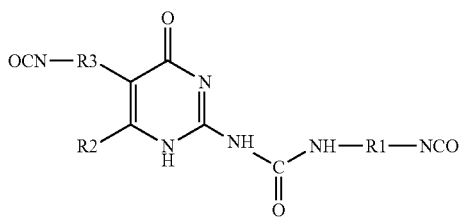

in which R1, R2 and R3 are as defined above, and in particular:
R1 represents -isophorone-, —(CH$_2$)$_2$—, —(CH$_2$)$_6$—, —CH$_2$CH(CH$_3$)—CH$_2$—C(CH$_3$)$_2$—CH$_2$—CH$_2$, 4,4'-methylenebiscyclohexylene or 2-methyl-1,3-phenylene; and/or
R2 represents H, CH$_3$, ethyl, C$_{13}$H$_{27}$, C$_7$H$_{15}$, phenyl, isopropyl, isobutyl, n-butyl, tert-butyl, n-propyl, or else —CH(C$_2$H$_5$)(C$_4$H$_9$); and/or
R3 represents a divalent radical —R'3-O—C(O)—NH—R'4- in which R'3 and R'4, which may be identical or different, represent a divalent carbon-based radical chosen from a linear or branched C$_1$-C$_{30}$ alkyl group, a C$_4$-C$_{12}$ cycloalkyl group and a C$_4$-C$_{12}$ aryl group; or mixtures thereof; and in particular R'3 represents a C$_1$-C$_4$ alkylene, in particular 1,2-ethylene, and R'4 represents the divalent radical derived from isophorone.

A junction group that is most particularly preferred is the one having the formula:

The compound according to the invention may be prepared via the processes usually employed by those skilled in the art for forming a urethane bond, between the free OH functions of the wax and the isocyanate functions borne by the junction group. By way of illustration, a general preparation process consists in:
heating the wax comprising at least one reactive function, in particular OH, to a temperature that may be between 60° C. and 140° C.;
adding the junction group bearing the reactive functions, in particular isocyanate;
optionally stirring the mixture, under a controlled atmosphere, at a temperature of about 100-130° C.; for 1 to 24 hours;
monitoring by infrared spectroscopy the disappearance of the characteristic band for isocyanates (between 2500 and 2800 cm$^{-1}$) so as to stop the reaction at the total disappearance of the peak, and then to allow the final product to cool to room temperature.

The reaction may be performed in the presence of a solvent, in particular methyltetrahydrofuran, tetrahydrofuran, toluene or butyl acetate. It is also possible to add a conventional catalyst for forming a urethane bond. An example that may be mentioned is dibutyltin dilaurate. The compound may finally be washed and dried, or even purified, according to the general knowledge of those skilled in the art.

According to another embodiment, the reaction may comprise the following steps: functionalization of the wax with a diisocyanate, and then reaction with 6-methylisocytosine or 5-hydroxyethyl-6-methylisocytosine. An illustration of such a reaction is given in Folmer et al., Adv. Mater, 12, 874-78 (2000).

It has been found that the use of the compounds according to the invention may lead, after application of the composition to keratin materials, to the formation of a supramolecular polymer in the form of a physically crosslinked network, in particular crosslinked by means of hydrogen bonds, which is generally in the form of a film, and which has very good mechanical strength.

For the purposes of the invention, the term "supramolecular polymer" means a polymer chain or network formed from the assembly of non-polymeric compounds according

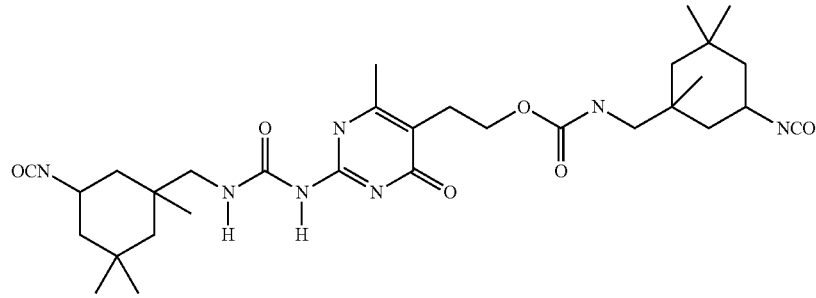

According to one particular embodiment of the invention, the junction groups may be attached to the wax via functionalization of the junction group with an isocyanate. According to another embodiment, it is possible to perform the reverse reaction by prefunctionalizing the wax with a diisocyanate.

As mentioned above, the compound according to the invention can therefore result from the chemical reaction between a wax and a junction group.

to the invention with at least one other identical or different non-polymeric compound according to the invention, each assembly comprising at least one pair of identical or different paired junction groups.

For the purposes of the invention, the term "pair of paired junction groups" means two junction groups, each of which may optionally be borne by the same compound according to the invention, the two groups being connected together via 4H bonds.

Thus, the supramolecular polymer will have points of physical crosslinking provided by the H bonds between these pairs of junction groups. The physical crosslinking will ensure the maintenance and persistence of the cosmetic effect in a similar manner to chemical crosslinking, while at the same time allowing reversibility, i.e. the possibility of totally removing the deposit.

The number-average molecular weight (Mn) of the compound according to the invention is preferably between 180 and 18,000, preferably from 200 to 15,000, or even from 300 to 10,000, even better still from 400 to 5000 and preferentially from 500 to 2500.

The compound according to the invention is advantageously soluble in the cosmetic oily media usually used, in particular in plant oils, $C_6$-$C_{32}$ alkanes, $C_8$-$C_{32}$ fatty esters, $C_2$-$C_7$ short esters, $C_8$-$C_{32}$ fatty alcohols, and more particularly in media comprising at least isododecane, Parleam, isononyl isononanoate, octyldodecanol, a $C_{12}$-$C_{15}$ alkyl benzoate, butyl acetate or ethyl acetate, alone or as a mixture. The term "soluble" means that the compound forms a clear solution in at least one solvent chosen from isododecane, Parleam, isononyl isononanoate, octyldodecanol, a $C_{12}$-$C_{15}$ alkyl benzoate, butyl acetate or ethyl acetate, in a proportion of at least 5% by weight, at 25° C.

The compounds according to the invention may be used advantageously in a cosmetic composition, which moreover comprises a cosmetically acceptable medium, i.e. a medium that is compatible with keratin materials such as facial or bodily skin, the eyelashes, the eyebrows, the lips and the nails.

The amount of compound present in the compositions obviously depends on the type of composition and on the desired properties, and it may vary within a very wide range, generally between 5% and 80% by weight, preferably between 10% and 75% by weight, in particular between 20% and 70% by weight, or even between 25% and 65% by weight, and better still between 30% and 60% by weight, relative to the weight of the final cosmetic composition.

The composition may thus comprise, depending on the intended application, constituents that are common for this type of composition.

The composition according to the invention may advantageously comprise a liquid fatty phase, which may constitute a solvent medium for the polymers according to the invention, and which may comprise at least one compound chosen from volatile or nonvolatile carbon-based, hydrocarbon-based, fluoro and/or silicone oils and/or solvents of mineral, animal, plant or synthetic origin, alone or as a mixture, provided that they form a stable, homogeneous mixture and are compatible with the intended use.

For the purposes of the invention, the term "volatile" means any compound that is capable of evaporating on contact with keratin materials, or the lips, in less than one hour, at ambient temperature (25° C.) and atmospheric pressure (1 atm). In particular, this volatile compound has a non-zero vapour pressure, at ambient temperature and atmospheric pressure, especially ranging from 0.13 Pa to 40,000 Pa ($10^{-3}$ to 300 mmHg), in particular ranging from 1.3 Pa to 13,000 Pa (0.01 to 100 mmHg), and more particularly ranging from 1.3 Pa to 1300 Pa (0.01 to 10 mmHg). In contrast, the term "nonvolatile" means a compound that remains on keratin materials or the lips at ambient temperature and atmospheric pressure for at least one hour and that in particular has a vapour pressure of less than $10^{-3}$ mmHg (0.13 Pa).

Preferably, the physiologically acceptable medium of the composition according to the invention may comprise, in a liquid fatty phase, at least one oil and/or solvent that may be chosen, alone or as a mixture, from:

1/esters of monocarboxylic acids with monoalcohols and polyalcohols; advantageously, said ester is a $C_{12}$-$C_{15}$ alkyl benzoate or corresponds to the following formula: $R'_1$—COO—$R'_2$ in which:

$R'_1$ represents a linear or branched alkyl radical of 1 to 40 carbon atoms and preferably of 7 to 19 carbon atoms, optionally comprising one or more ethylenic double bonds, optionally substituted, and the hydrocarbon-based chain of which may be interrupted with one or more heteroatoms chosen from N and O and/or one or more carbonyl functions, and $R'_2$ represents a linear or branched alkyl radical of 1 to 40 carbon atoms, preferably of 3 to 30 carbon atoms and better still of 3 to 20 carbon atoms, optionally comprising one or more ethylenic double bonds, optionally substituted, and the hydrocarbon-based chain of which may be interrupted with one or more heteroatoms chosen from N and O and/or one or more carbonyl functions.

The term "optionally substituted" means that $R'_1$ and/or $R'_2$ may bear one or more substituents chosen, for example, from groups comprising one or more heteroatoms chosen from O and/or N, such as amino, amine, alkoxy or hydroxyl.

Examples of groups $R'_1$ are those derived from fatty acids, preferably higher fatty acids chosen from the group formed from acetic acid, propionic acid, butyric acid, caproic acid, caprylic acid, pelargonic acid, capric acid, undecanoic acid, lauric acid, myristic acid, palmitic acid, stearic acid, isostearic acid, arachidic acid, behenic acid, oleic acid, linolenic acid, linoleic acid, oleostearic acid, arachidonic acid and erucic acid, and mixtures thereof.

Preferably, $R'_1$ is an unsubstituted branched alkyl group of 4 to 14 carbon atoms and preferably of 8 to 10 carbon atoms and $R_2$ is an unsubstituted branched alkyl group of 5 to 15 carbon atoms and preferably of 9 to 11 carbon atoms.

Mention may be made in particular, preferably, of $C_8$-$C_{48}$ esters, optionally incorporating in their hydrocarbon-based chain one or more heteroatoms from among N and O and/or one or more carbonyl functions; and more particularly purcellin oil (cetostearyl octanoate), isononyl isononanoate, isopropyl myristate, isopropyl palmitate, 2-ethylhexyl palmitate, 2-octyldodecyl stearate, 2-octyldodecyl erucate, isostearyl isostearate, $C_{12}$ to $C_{15}$ alkyl benzoate, hexyl laurate, diisopropyl adipate; and heptanoates, octanoates, decanoates or ricinoleates of alcohols or of polyalcohols, for example of fatty alcohols, for instance propylene glycol dioctanoate, and also isopropyl N-lauroyl sarcosinate (especially Eldew-205SL from Ajinomoto); hydroxylated esters, for instance isostearyl lactate, diisostearyl malate; and pentaerythritol esters; branched $C_8$-$C_{16}$ esters, in particular isohexyl neopentanoate;

2/hydrocarbon-based plant oils with a high triglyceride content formed from fatty acid esters of glycerol, the fatty acids of which may have varied chain lengths from $C_4$ to $C_{24}$, these chains possibly being linear or branched, and saturated or unsaturated; these oils are in particular wheat germ oil, corn oil, sunflower oil, shea oil, castor oil, sweet almond oil, macadamia oil, apricot oil, soybean oil, rapeseed oil, cottonseed oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passionflower oil, musk rose oil, jojoba oil, palm oil or beauty-leaf oil; or caprylic/capric acid triglycerides, such as those sold by the company Stearinerie Dubois or those sold under the names Miglyol 810®, 812® and 818® by the company Dynamit Nobel;

3/ $C_6$-$C_{32}$ and in particular $C_{12}$-$C_{26}$ alcohols, and in particular monoalcohols, for instance oleyl alcohol, linoleyl alcohol, linolenyl alcohol, isostearyl alcohol, 2-hexyldecanol, 2-butyloctanol, 2-undecylpentadecanol and octyldodecanol;

4/linear or branched, volatile or nonvolatile hydrocarbon-based oils, of synthetic or mineral origin, which may be chosen from hydrocarbon-based oils containing from 5 to 100 carbon atoms, and in particular petroleum jelly, polydecenes, hydrogenated polyisobutenes such as Parleam, squalane and perhydrosqualene, and mixtures thereof.

Mention may be made more particularly of linear, branched and/or cyclic $C_5$-$C_{48}$ alkanes, and preferentially branched $C_8$-$C_{16}$ alkanes, for instance $C_8$-$C_{16}$ isoalkanes of petroleum origin (also known as isoparaffins); in particular decane, heptane, dodecane and cyclohexane; and also isododecane, isodecane and isohexadecane;

5/volatile or nonvolatile silicone oils.

Volatile silicone oils that may be mentioned include volatile linear or cyclic silicone oils, in particular those with a viscosity of less than 8 centistokes, and in particular containing from 2 to 10 silicon atoms, these silicones optionally comprising alkyl or alkoxy groups containing from 1 to 22 carbon atoms; and in particular octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and methylhexyldimethylsiloxane, and mixtures thereof.

The nonvolatile silicone oils that may be used according to the invention may be polydimethylsiloxanes (PDMSs), polydimethylsiloxanes comprising alkyl or alkoxy groups, which are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and 2-phenylethyl trimethylsiloxysilicates.

Preferentially, the physiologically acceptable medium of the composition according to the invention comprises, in a liquid fatty phase, at least one oil and/or solvent chosen from, alone or as a mixture, isododecane, Parleam, isononyl isononanoate, octyldodecanol, phenyl trimethicone, $C_{12}$-$C_{15}$ alkyl benzoates, butyl and ethyl acetates, and/or D5 (decamethylcyclopentasiloxane).

The liquid fatty phase may also comprise additional oils and/or solvents, which may be chosen, alone or as a mixture, from:
  fluoro oils such as perfluoropolyethers, perfluoroalkanes such as perfluorodecalin, perfluoroadamantanes, perfluoroalkyl phosphate monoesters, diesters and triesters, and fluoro ester oils;
  oils of animal origin;
  $C_6$ to $C_{40}$ and in particular $C_{10}$-$C_{40}$ ethers; propylene glycol ethers that are liquid at ambient temperature, such as propylene glycol monomethyl ether, propylene glycol monomethyl ether acetate and dipropylene glycol mono-n-butyl ether;
  $C_8$-$C_{32}$ fatty acids, for instance oleic acid, linoleic acid and linolenic acid, and mixtures thereof;
  difunctional oils, comprising two functions chosen from ester and/or amide and comprising from 6 to 30 carbon atoms, in particular 8 to 28 carbon atoms and better still 10 to 24 carbon atoms, and 4 heteroatoms chosen from O and N; preferably, the amide and ester functions being in the chain;
  ketones that are liquid at ambient temperature (25° C.), such as methyl ethyl ketone, methyl isobutyl ketone, diisobutyl ketone, isophorone, cyclohexanone and acetone;
  aldehydes that are liquid at ambient temperature, such as benzaldehyde and acetaldehyde.

The liquid fatty phase may represent 1% to 90% by weight of the composition, especially from 5% to 75% by weight, in particular from 10% to 60% by weight, or even from 25% to 55% by weight, of the total weight of the composition.

The composition according to the invention may advantageously comprise a thickener which can in particular be chosen from:
  silicas, in particular hydrophobic silicas, such as those described in document EP-A-898960, and for example sold under the references Aerosil R812® by the company Degussa, Cab-O-Sil TS-530®, Cab-O-SIL TS-610® and Cab-O-Sil TS-720® by the company Cabot, and Aerosil R972® and Aerosil R974® by the company Degussa;
  clays, such as montmorillonite, modified clays such as bentones for example, stearalkonium hectorite, stearalkonium bentonite;
  polysaccharide alkyl ethers (in particular of which the alkyl group comprises from 1 to 24 carbon atoms, preferably from 1 to 10, better still from 1 to 6, more especially from 1 to 3), such as those described in document EP-A-898958.

The total proportion of thickener in the composition according to the invention can range from 0.05% to 40% by weight, relative to the total weight of the composition, preferably from 0.5% to 20% by weight and better still from 1% to 15% by weight.

The composition according to the invention may also comprise at least one wax of plant, animal, mineral or synthetic origin, or even a silicone wax.

Mention may be made in particular, alone or as a mixture, of hydrocarbon-based waxes such as beeswax; carnauba wax, candelilla wax, ouricury wax, Japan wax, cork fibre wax or sugarcane wax; paraffin wax, lignite wax; microcrystalline waxes; lanolin wax; montan wax; ozokerites; polyethylene waxes; waxes obtained by Fischer-Tropsch synthesis; hydrogenated oils, fatty esters and glycerides that are solid at 25° C. It is also possible to use silicone waxes, among which mention may be made of alkyl or alkoxy polymethylsiloxanes and/or polymethylsiloxane esters. The amount of wax in the composition according to the invention can range from 0.1% to 70% by weight, relative to the total weight of the composition, preferably from 1% to 40% by weight and better still from 5% to 30% by weight.

The composition according to the invention may also comprise one or more colorants chosen from pulverulent compounds, for instance pigments, fillers, nacres and glitter flakes, and/or liposoluble or water-soluble dyes.

The colorants, in particular pulverulent colorants, may be present in the composition in a content of from 0.01% to 50% by weight, preferably from 0.1% to 40% by weight or even from 1% to 30% by weight relative to the weight of the composition. The term "pigments" should be understood as meaning white or coloured, mineral or organic particles of any shape, which are insoluble in the physiological medium, and which are intended to colour the composition.

The term "nacres" should be understood as meaning iridescent particles of any shape, in particular produced by certain molluscs in their shell, or else synthesized.

The pigments may be white or coloured, mineral and/or organic, and interference or non-interference pigments. Among the mineral pigments that may be mentioned are titanium dioxide, optionally surface-treated, zirconium oxides or cerium oxides, and also iron oxides or chromium oxides, manganese violet, ultramarine blue, chromium hydrate and ferric blue. Among the organic pigments that may be mentioned are carbon black, pigments of D & C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica with iron oxides, titanium mica in particular with ferric blue or with chromium oxide, titanium mica with an organic pigment of the above-mentioned type, and also nacreous pigments based on bismuth oxychloride.

The fillers may be mineral or organic, and lamellar or spherical. Mention may be made of talc, mica, silica, kaolin, Nylon powder and polyethylene powder, poly-β-alanine powder and polyethylene powder, Teflon, lauroyllysine, starch, boron nitride, powders of tetrafluoroethylene polymers, hollow microspheres such as Expancel (Nobel Industrie), Polytrap (Dow Corning), precipitated calcium carbonate, magnesium carbonate, magnesium hydrocarbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The lipsoluble dyes are, for example, Sudan red, DC Red 17, DC Green 6, β-carotene, soybean oil, Sudan brown, DC Yellow 11, DC Violet 2, DC Orange 5 and quinoline yellow. They may represent 0.01% to 20% and better still from 0.1% to 6% of the weight of the composition.

The water-soluble dyes are, for example, beetroot juice or methylene blue, and may represent from 0.01% to 6% of the total weight of the composition.

The composition may also comprise other ingredients commonly used in cosmetic compositions. Such ingredients may be chosen from antioxidants, fragrances, essential oils, preservatives, cosmetic active agents, moisturizers, vitamins, ceramides, sunscreens, surfactants, gelling agents, spreading agents, wetting agents, dispersants, antifoams, neutralizing agents, stabilizers, polymers and in particular liposoluble film-forming polymers, and mixtures thereof.

Needless to say, those skilled in the art will take care to select this or these optional additional compound(s) and/or the amounts thereof so that the advantageous properties of the composition for the use according to the invention are not, or not substantially, adversely affected by the envisaged addition.

The compositions according to the invention may be in any common acceptable form for a cosmetic composition. They may thus be in the form of a suspension or a dispersion, in particular of oil in water by means of vesicles; an optionally thickened or even gelled organic or oily solution; an oil-in-water, water-in-oil or multiple emulsion; a gel or a mousse; an oily or emulsified gel; a dispersion of vesicles, in particular lipid vesicles; a two-phase or multiphase lotion; a spray; a lotion, a cream, a salve, a soft paste, an ointment, a solid that has been cast or moulded in particular as a stick or in a dish, or a compacted solid.

Those skilled in the art may select the appropriate galenical form, and also the method for preparing it, on the basis of their general knowledge, taking into account firstly the nature of the constituents used, in particular their solubility in the support, and secondly the intended application of the composition.

The compositions in accordance with the invention may be used for caring for or making up keratin materials such as the skin, the eyelashes, the eyebrows, the nails, the lips or the hair, and more particularly for making up the lips, the eyelashes and/or the face.

They may thus be in the form of a product for caring for and/or making up bodily or facial skin, the lips, the eyelashes, the eyebrows, the hair or the nails; an antisun or self-tanning product; or a hair product; they may advantageously be in the form of a makeup composition, in particular a mascara, an eyeliner, a lipstick, a lip gloss, a face powder, an eyeshadow, a foundation, a nail varnish or a nailcare product.

A subject of the invention is also a cosmetic process for treating keratin materials, in particular bodily or facial skin, the lips, the nails the eyelashes and/or the hair, comprising the application to said materials of a cosmetic composition as defined previously.

This process according to the invention in particular allows said keratin materials, in particular the lips and/or the nails, to be cared for or made up, by applying a composition, in particular a lipstick, a foundation or a mascara according to the invention.

The invention is illustrated in greater detail in the following exemplary embodiments.

EXAMPLE 1

13 g of beeswax are heated as a mixture with 11 mg of dibutyltin dilaurate (catalyst) and 0.93 g of methylisocytosine. The mixture is heated to 100° C. and placed under vacuum for 2 hours. The mixture is then brought down to 70° C., under argon, and 1.5 g of isophorone diisocyanate are added; mixing is carried out while leaving under argon for 2 hours at 70° C.

2.5 ml of anhydrous propylene carbonate are then added, and the temperature of the reaction medium is increased to 140° C., under argon and with stirring for 3 hours at this temperature. The disappearance of the isocyanate functions is monitored by infrared spectroscopy, until complete disappearance of the characteristic peak at 2250 $cm^{-1}$. The temperature of the mixture is then brought back to 70° C., and 60 ml of tetrahydrofuran and 5 ml of ethanol are added, followed by stirring for 30 minutes. The reaction mixture is filtered over celite, precipitated from ethanol and dried under reduced pressure.

The desired functionalized wax is obtained in the form of a white wax.

Observations:
beeswax at 23%, in isododecane: the mixture is white and compact; after hot deposition on a glass plate and cooling to 25° C., it is observed that it forms a non-cohesive, tacky white deposit. To the touch, the finger sinks into the deposit; it has a fatty feel;

functionalized beeswax prepared above, at 23%, in isododecane: the mixture is white and compact; after hot deposition on a glass plate and cooling to 25° C., it is observed that it forms a brittle non-cohesive deposit after evaporation of the isododecane. No fatty sensation is felt; on the contrary, it is dry to the touch; the finger does not sink into the deposit.

EXAMPLE 2

A lipstick is prepared, comprising (% by weight):

| | |
|---|---|
| functionalized beeswax prepared in example 1 | 10% |
| isododecane | 40% |
| cyclopentapolysiloxane | 10% |
| hydrogenated polyisobutene | 30% |
| pigments | 10% |

EXAMPLE 3

19.3 g of cetyl alcohol are heated under reduced pressure, at 60° C., and after two hours, 10 ml of anhydrous butyl acetate are added; the mixture is brought to 40° C., still under a controlled atmosphere. 18.9 g of IPDI (isophorone diisocyanate) are then added, followed by a further 10 ml of butyl acetate, and 9 mg of catalyst (dibutyltin dilaurate). The reaction medium is stirred for 16 hours at 40° C. under a controlled atmosphere. 12.73 g of methyl isocytosine and 20 ml of anhydrous propylene carbonate are then added, and the mixture is brought to 140° C., and the temperature maintained for 2 h 30 min. The disappearance of the isocyanates is monitored by IR spectroscopy and, after complete disappearance of the characteristic isocyanate peak (2250 cm$^{-1}$), stirring is maintained for a further 30 min. The reaction medium is brought to 70° C., diluted with 200 ml of hexane and filtered over celite. This organic phase is washed three times with a mixture of H$_2$O/ethanol (2/1) saturated with NaCl, and then dried over Na$_2$SO$_4$, filtered and dried under reduced pressure. The desired product is obtained in the form of a brittle solid.

The invention claimed is:

1. Cosmetic composition comprising, in a cosmetically acceptable medium, a compound obtained by reaction between:
   at least one wax bearing at least one reactive function chosen from OH or COOH, wherein said at least one wax is at least one member selected from the group consisting of
   candelilla wax, carnauba wax, sugarcane wax; beeswax, montan wax, and jojoba wax; and
   at least one junction group capable of establishing hydrogen bonds with one or more partner junction groans, each pairing of a unction group involving at least 4 hydrogen bonds, said junction group bearing at least one "complementary" reactive function capable of reacting with the reactive function borne by the wax, said junction group comprising at least one unit of formula (I) or (II):

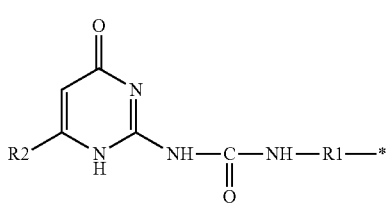

(I)

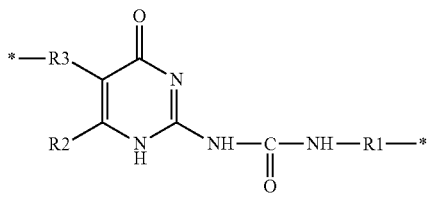

(II)

in which:
R1 and R3, which may be identical or different, represent a divalent carbon-based radical chosen from (i) a linear or branched C$_1$-C$_{32}$ alkyl group, (ii) a C$_4$-C$_{16}$ cycloalkyl group and (iii) a C$_4$-C$_{16}$ aryl group; optionally comprising 1 to 8 heteroatoms chosen from O, N, S, F, Si and P; and/or optionally substituted with an ester or amide function or with a C$_1$-C$_{12}$ alkyl radical; or a mixture of these groups;

R2 represents a hydrogen atom or a linear, branched or cyclic, saturated or unsaturated, optionally aromatic, C$_1$-C$_{32}$ carbon-based (alkyl) radical, which may comprise one or more heteroatoms chosen from O, N, S, F, Si and P.

2. Composition according to claim 1, in which the unit is of formula (I):
   with R1=-isophorone-, R2=methyl, which gives the unit of formula:

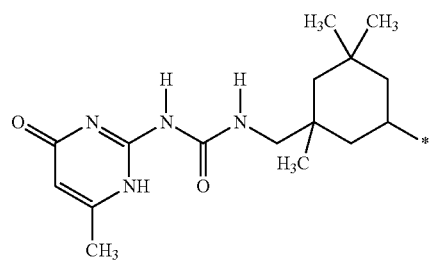

with R1=—(CH$_2$)$_6$—, R2=methyl, which gives the unit of formula:

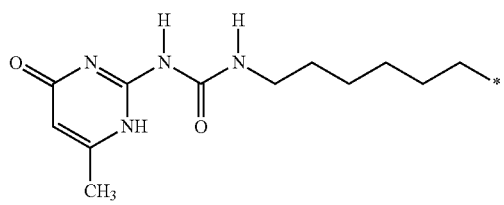

with R1=—(CH$_2$)$_6$—, R2=isopropyl, which gives the of formula:

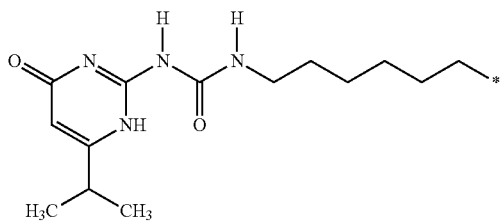

or
with R1=4,4'-methylenebiscyclohexylene and R2=methyl, which gives the unit of formula:

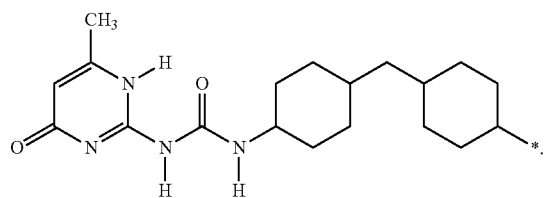

3. Composition according to claim 1, in which the junction group is chosen from the following groups:

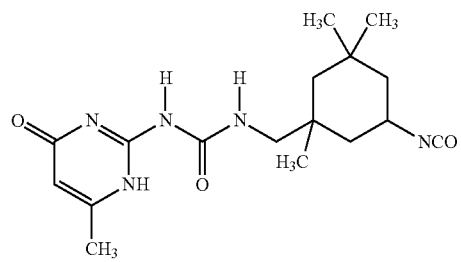
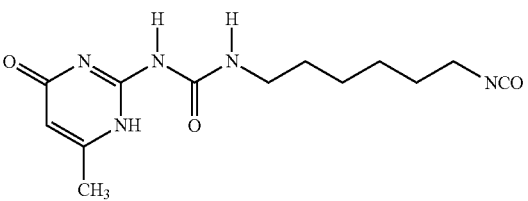

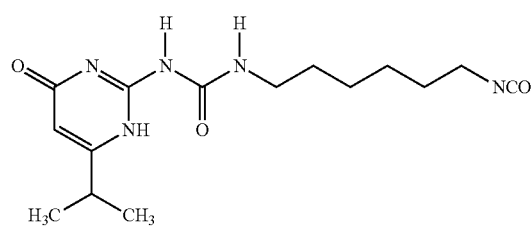
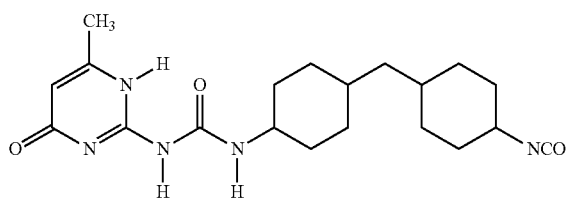

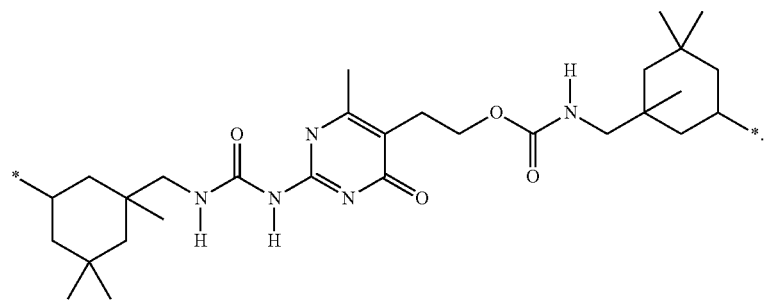

4. Composition according to claim 1, in which the compound is present in an amount of between 5% and 80% by weight relative to the weight of the final cosmetic position.

5. Composition according to claim 1, comprising at least one constituent chosen from carbon-based, hydrocarbon-based, fluoro and/or silicone oils and/or solvents of mineral, animal, plant or synthetic origin; thickeners; waxes of plant, animal, mineral or synthetic origin, or silicone waxes; colorants; antioxidants, fragrances, essential oils, preservatives, cosmetic active agents, moisturizers, vitamins, ceramides, sunscreens, surfactants, gelling agents, spreading agents, wetting agents, dispersants, antifoams, neutralizing agents, stabilizers, polymers, and mixtures thereof.

6. Composition according to claim 1, which is in the form of a product for caring for and/or making up bodily or facial skin, the lips, the eyelashes, the eyebrows, the hair or the nails; an anti-sun or self-tanning product; or a hair product.

7. Cosmetic process for treating keratin materials, in particular bodily or facial skin, the lips, the nails, the eyelashes and/or the hair, comprising the application to said materials of a cosmetic composition as defined in claim 1.

8. Compound obtained by reaction between:
at least one wax bearing at least one reactive function chosen from OH, COOH or anhydride, wherein said at least one wax is at least one member selected from the group consisting of candelilla wax, carnauba wax, sugarcane wax; beeswax, montan wax, and jojoba wax; and at least one junction group capable of establishing hydrogen bonds with one or more partner junction groups, each pairing of a junction group involving at least 4 hydrogen bonds, said junction group bearing at least one "complementary" reactive function capable of reacting with the reactive function borne by the wax, said junction group comprising at least one unit of formula (I) or (II):

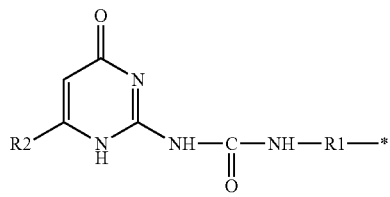

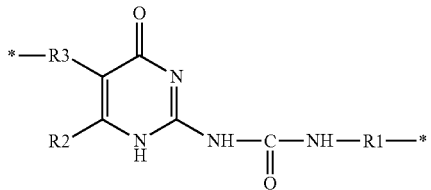

in which:

R1 and R3, which may be identical or different, represent a divalent carbon-based radical chosen from (i) a linear or branched $C_1$-$C_{32}$ alkyl group, (ii) a $C_4$-$C_{16}$ cycloalkyl group and (iii) a $C_4$-$C_{16}$ aryl group: optionally comprising 1 to 8 heteroatoms chosen from O, N, S, F, Si and P; and/or optionally substituted with an ester or amide function or with a $C_1$-$C_{12}$ alkyl radical; or a mixture of these groups;

R2 represents a hydrogen atom or a linear, branched or cyclic, saturated or unsaturated, optionally aromatic, $C_1$-$C_{32}$ carbon-based (alkyl) radical, which may comprise one or more heteroatoms chosen from O, N, S, F, Si and P.

9. Composition according to claim 2, in which the junction group is chosen from the following groups:

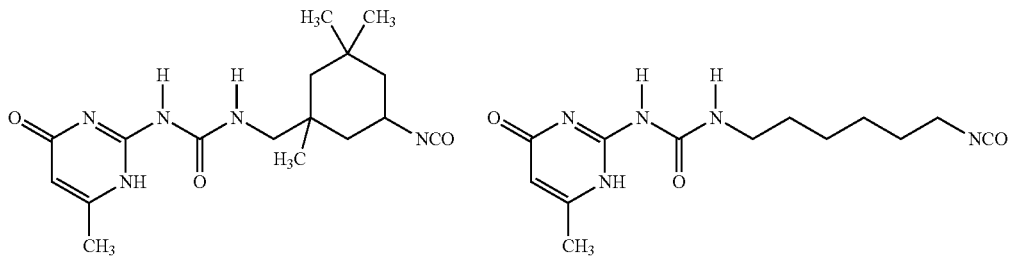

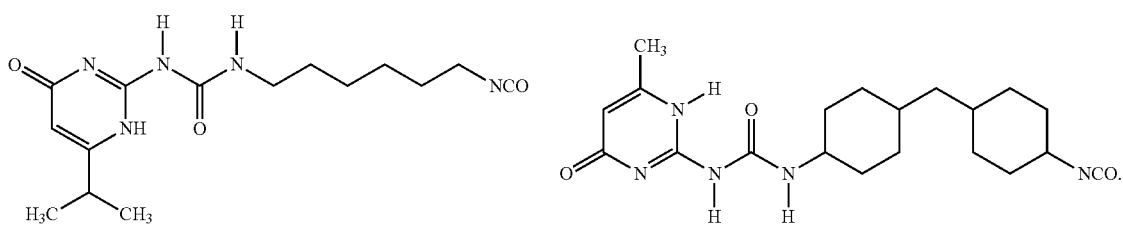

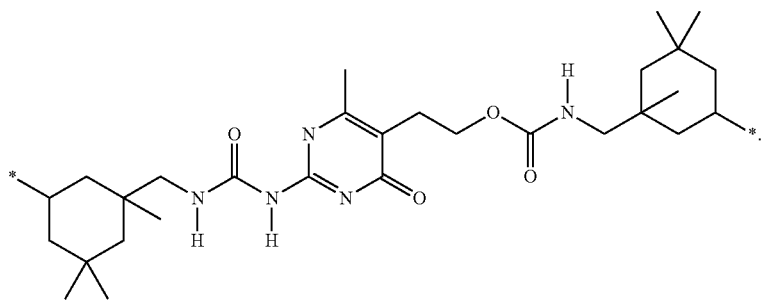

10. Composition according to claim 2, in which the compound is present in an amount of between 5% and 80% by weight relative to the weight of the final cosmetic composition.

11. Composition according to claim 1, wherein said at least one wax bearing at least one reactive function chosen from OH or COOH, is selected from the group consisting of carnauba wax, beeswax, jojoba wax, and mixtures thereof.

12. Composition according to claim 8, wherein said at least one wax bearing at least one reactive function chosen from OH, COOH or anhydride, is selected from the group consisting of carnauba wax, beeswax, jojoba wax, and mixtures thereof.

13. Composition according to claim 1, wherein said at least one wax bearing at least one reactive function chosen from OH or COOH, is beeswax.

14. Composition according to claim 2, wherein said at least one wax bearing at least one reactive function chosen from OH or COOH, is beeswax.

15. Composition according to claim 3, wherein said at least one wax bearing at least one reactive function chosen from OH or COOH, is beeswax.

16. Composition according to claim 4, wherein said at least one wax bearing at least one reactive function chosen from OH or COOH, is beeswax.

17. Composition according to claim 5, wherein said at least one wax bearing at least one reactive function chosen from OH or COOH, is beeswax.

18. Composition according to claim 8, wherein said at least one wax bearing at least one reactive function chosen from OH or COOH, is beeswax.

19. Composition according to claim 9, wherein said at least one wax bearing at least one reactive function chosen from OH or COOH, is beeswax.

* * * * *